(12) United States Patent
Lee et al.

(10) Patent No.: US 8,222,045 B2
(45) Date of Patent: Jul. 17, 2012

(54) MICROFLUIDIC DEVICE USING CENTRIFUGAL FORCE, METHOD OF MANUFACTURING THE MICROFLUIDIC DEVICE AND SAMPLE ANALYZING METHOD USING THE MICROFLUIDIC DEVICE

(75) Inventors: Yang-ui Lee, Seoul (KR); Yoon-kyoung Cho, Suwon-si (KR); Jeong-gun Lee, Seoul (KR); Do-gyoon Kim, Yongin-si (KR); Han-sang Kim, Osan-si (KR); Jong-myeon Park, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 151 days.

(21) Appl. No.: 12/570,414

(22) Filed: Sep. 30, 2009

(65) Prior Publication Data

US 2010/0093105 A1 Apr. 15, 2010

(30) Foreign Application Priority Data

Oct. 14, 2008 (KR) .................. 10-2008-0100763
Jul. 13, 2009 (KR) .................. 10-2009-0063456

(51) Int. Cl.
*G01N 21/00* (2006.01)
*G01N 21/61* (2006.01)
*G01N 33/00* (2006.01)
*B32B 37/12* (2006.01)

(52) U.S. Cl. ........ 436/180; 436/174; 436/141; 436/164; 422/68.1; 422/50; 156/275.5; 156/272.2; 156/60; 156/1

(58) Field of Classification Search .................. 436/180, 436/174, 141, 164; 422/68.1, 50; 156/275.5, 156/272.2, 60, 1
See application file for complete search history.

(56) References Cited

U.S. PATENT DOCUMENTS

| | | | | |
|---|---|---|---|---|
| 6,582,662 | B1 * | 6/2003 | Kellogg et al. | 422/72 |
| 2003/0175162 | A1 * | 9/2003 | Anazawa et al. | 422/99 |
| 2004/0203136 | A1 * | 10/2004 | Kellogg et al. | 435/287.2 |
| 2005/0148091 | A1 * | 7/2005 | Kitaguchi et al. | 436/164 |
| 2006/0051248 | A1 * | 3/2006 | Cho et al. | 422/100 |
| 2009/0238724 | A1 * | 9/2009 | Yamamoto et al. | 422/68.1 |

FOREIGN PATENT DOCUMENTS

WO WO 2007/052648 * 5/2007

* cited by examiner

*Primary Examiner* — Christine T Mui
(74) *Attorney, Agent, or Firm* — Sughrue Mion, PLLC

(57) ABSTRACT

Provided is a microfluidic device including: a sample chamber; at least one analyzing unit receiving a sample from the sample chamber and detecting components contained in the sample according to a reaction of the sample and a reagent; and a denaturation detection chamber determining the storage condition of the microfluidic device, wherein the denaturation detection chamber accommodates a material whose light absorption changes according to the temperature and the water thereof.

37 Claims, 9 Drawing Sheets

MICROFLUIDIC DEVICE USING CENTRIFUGAL FORCE, METHOD OF MANUFACTURING THE MICROFLUIDIC DEVICE AND SAMPLE ANALYZING METHOD USING THE MICROFLUIDIC DEVICE

CROSS-REFERENCE TO RELATED APPLICATIONS

This application claims the benefit of Korean Patent Application No. 10-2008-0100763, filed on Oct. 14, 2008, and Korean Patent Application No. 10-2009-0063456, filed on Jul. 13, 2009, in the Korean Intellectual Property Office, the disclosure of which is incorporated herein in its entirety by reference.

BACKGROUND

1. Field

One or more embodiments relate to a microfluidic device using centrifugal force, method of manufacturing the microfluidic device and a method of analyzing a sample using the microfluidic device.

2. Description of the Related Art

Examples of microfluidic structures of a microfluidic device include a chamber which can accommodate a small amount of fluid, a channel through which the fluid can flow, a valve which can adjust the flow of the fluid, and various functional units which can accommodate the fluid and conduct predetermined functions. A small chip on which the microfluidic structures of a microfluidic device are mounted in order to perform various tests including a biochemical reaction is referred to as a biochip, and in particular, a device which is formed to perform various operations in one chip is referred to as a lab-on-a-chip.

Driving pressure is required to transport a fluid within the microfluidic structures of the microfluidic device, and a capillary pressure or pressure provided by a pump is used as the driving pressure. Recently, microfluidic devices using centrifugal force by mounting microfluidic structures in a disk-shaped platform have been suggested. These devices are referred to as a lab-on-a-disk or a lab CD.

SUMMARY

One or more embodiments include a microfluidic device using centrifugal force, which measures light absorption of a reactant material of a sample and a reagent to analyze components of the sample.

One or more embodiments include a method of manufacturing a microfluidic device using centrifugal force by bonding multiple layers using an adhesive.

One or more embodiments include a method of analyzing a sample by reacting a sample with a reagent using the microfluidic device using centrifugal force and measuring the light absorption of the reactant material and detecting components of the sample.

Additional aspects and/or advantages will be set forth in part in the description which follows and, in part, will be apparent from the description, or may be learned by practice of the invention.

To achieve the above and/or other aspects and advantages, one or more embodiments may include a microfluidic device including: a sample chamber; at least one analyzing unit receiving a sample from the sample chamber and detecting components contained in the sample according to a reaction between the sample and a reagent; and a denaturation detection chamber determining the storage condition of the microfluidic device, wherein the denaturation detection chamber accommodates a material whose light absorption changes according to the temperature and/or the water content thereof.

The at least one analyzing unit may include: a sample distributing unit connected to the sample chamber and separating supernatant from the sample; a supernatant metering chamber having a capacity for metering the supernatant supplied from the sample distributing unit; a dilution chamber connected to the supernatant metering chamber, wherein the dilution chamber accommodates a diluent for diluting the supernatant; and a plurality of reaction chambers connected to the dilution chamber via a distribution channel to receive a sample diluent, wherein the reaction chambers accommodate a reagent.

The microfluidic device may further include a usage detection chamber to determine whether the microfluidic device has been used before or not by measuring light absorption of the usage detection chamber, wherein the usage detection chamber is disposed at an end of the sample distributing unit.

The microfluidic device may further include an excess sample chamber to determine the amount of the sample by measuring light absorption of the excess sample chamber and accommodating an excess amount of the sample exceeding the capacity of the sample distributing unit.

The microfluidic device may further include a supernatant detection chamber to determine the state of the supernatant by measuring light absorption of the supernatant detection chamber. The supernatant detection chamber is connected to a channel connecting the supernatant metering chamber and the sample distributing unit in order to receive supernatant.

The microfluidic device may further include an excess supernatant chamber that is connected to a channel connecting the supernatant metering chamber and the sample distributing unit, and accommodates an excessive amount of supernatant exceeding the capacity of the supernatant metering chamber.

The microfluidic device may further include at least one first concentration detection chamber, which provides a reference value for detecting concentration of the sample diluent by measuring light absorption of the first concentration detection chamber and receives supernatant from the sample distributing unit. The microfluidic device may include at least two of the first concentration detecting chambers, wherein the depths of the at least two first concentration detecting chambers are different.

The microfluidic device may further include a second concentration detection chamber that receives a sample diluent from the dilution chamber and is connected to the distribution channel so as to receive the sample diluent prior to the plurality of reaction chambers, wherein the second concentration detection chamber is a second chamber from the dilution chamber, and is used to detect concentration of the sample diluent by measuring the light absorption of the second concentration detection chamber.

The microfluidic device may further include a sample diluent detection chamber that receives a sample diluent and is connected to the distribution channel so as to receive the sample diluent lastly after all other reaction chambers receive the sample diluent.

The microfluidic device may further include a temperature detection chamber accommodating a material whose light absorption changes according to the temperature thereof.

The microfluidic device may further include a plurality of reagent cartridges accommodating the reagent in a lyophilized state and installed in the plurality of the reaction chambers.

The microfluidic device may further include a platform comprising a first layer and a second layer which are bonded to face each other; and an adhesive disposed between the first layer and the second layer to bond the first layer and the second layer to each other. The sample chamber, the at least one analyzing unit and the denaturation detection chamber may be formed as grooves in the first layer.

The adhesive may be cured by irradiation of an electromagnetic wave having a long wavelength. The adhesive may be cured by absorbing light having wavelength of about 200 nm to about 900 nm. The adhesive may also be cured by absorbing light having wavelength of about 250 nm to about 600 nm.

The adhesive may include a curing resin and a photopolymerization initiator. The photopolymerization initiator may be selected from the group consisting of benzoin ethers, benzophenonic materials, aminic materials, acetophenonic materials, thioxanthonic materials, Lewis acidic materials, and a combination thereof. The photopolymerization initiator may also be selected from the group consisting of camphor quinine, α-naphtyhl, benzyl, 2,4-diethylthioxantone, trimethylbenzoyl diphenylsulfineoxide, methylthioxantone, and a combination thereof To achieve the above and/or other aspects and advantages, one or more embodiments may include a method of manufacturing the microfluidic device, the method including: providing a first layer comprising grooves which correspond to the sample chamber, the at least one analyzing unit, and the denaturation detection chamber, respectively; providing a second layer; applying an adhesive on the first layer and/or the second layer; attaching the first layer and the second layer to each other; and curing the adhesive by irradiating light to the adhesive.

To achieve the above and/or other aspects and advantages, one or more embodiments may include a method of analyzing components contained in a sample using a microfluidic device including: a sample chamber; and at least one analyzing unit receiving a sample from the sample chamber and reacting the sample with a reagent, and measuring a light absorption of the reactant material in order to detect components contained in the sample, the method including: supplying a sample to the sample chamber of the microfluidic device; mounting the microfluidic device on a rotation driving unit; and determining whether the storage condition of the microfluidic device is appropriate for a test by measuring the light absorption of a denaturation detection chamber of the microfluidic device, in which a material whose light absorption changes according to the temperature and the water content thereof is accommodated.

The method may include: moving a sample from the sample chamber to a sample distributing unit by centrifugal force by rotating the microfluidic device using the rotation driving unit; and determining whether the microfluidic device has been used before by measuring the light absorption of the usage detection chamber disposed at an end of the sample distributing unit.

The method may include: moving a sample from the sample chamber to a sample distributing unit by centrifugal force by rotating the microfluidic device using the rotation driving unit; and determining whether the amount of the sample is sufficient by measuring the light absorption of the excess sample chamber which accommodates an excessive sample exceeding the capacity of the sample distributing unit.

When the microfluidic device includes a plurality of serial analyzing units that receive a sample from the sample chamber, a sample exceeding the capacity of the sample distributing unit of the last final analyzing unit of the plurality of analyzing units may be accommodated in the excess sample chamber.

The method may include determining whether the temperature of the microfluidic device is suitable for a test by measuring the light absorption of the temperature detection chamber which accommodates a material whose light absorption changes according to the temperature thereof, wherein the determining is performed using a detector.

The method may include: moving a sample from the sample chamber to a sample distributing unit by centrifugal force by rotating the microfluidic device using the rotation driving unit, and centrifugally separating supernatant from the sample accommodated in the sample distributing unit; and detecting at least one of an index indicating the status of the supernatant and whether a valve disposed at an exit of the sample distributing unit has an operational defect by measuring the light absorption of the supernatant detection chamber which receives supernatant from the sample distributing unit.

The method may include: metering a fixed amount of supernatant by moving supernatant from the sample distributing unit to the supernatant metering chamber; moving the supernatant exceeding the capacity of the supernatant metering chamber to the excess supernatant chamber; and determining whether the amount of the supernatant is sufficient by measuring a light absorption of the excess supernatant chamber.

The method may include: moving a sample from the sample chamber to a sample distributing unit by centrifugal force, that is, by rotating the microfluidic device using the rotation driving unit, and centrifugally separating supernatant from the sample accommodated in the sample distributing unit; measuring a light absorption of at least one first concentration detecting chamber which receives supernatant from the sample distributing unit; and forming a sample diluent by mixing the supernatant with a diluent accommodated in the dilution chamber; supplying via a distribution channel the sample diluent to a second concentration detection chamber, which is located at least in a second position from the dilution chamber among chambers connected to the dilution chamber via the distribution channel, and measuring light absorption of the second concentration detection chamber; and determining whether the dilution ratio of the sample diluent is appropriate according to the light absorption and depths (lengths) of the first and second concentration detection chambers.

The method may include: moving a sample from the sample chamber to a sample distributing unit by centrifugal force by rotating the microfluidic device using the rotation driving unit, and centrifugally separating supernatant from the sample accommodated in the sample distributing unit; forming a sample diluent by mixing the supernatant with the diluent accommodated in the dilution chamber; supplying via a distribution channel the sample diluent to a second concentration detection chamber, a plurality of reaction chambers accommodating a reagent, and a sample diluent detection chamber, which are sequentially disposed; and determining the uniformity of the dilution ratio of the sample diluent by measuring the light absorption of the second concentration detection chamber and the light absorption of at least one of the sample diluent detection chamber and a reaction chamber disposed at the end of the plurality of reaction chambers.

The method may include: moving a sample from the sample chamber to a sample distributing unit by centrifugal force by rotating the microfluidic device using the rotation driving unit, and centrifugally separating supernatant from the sample accommodated in the sample distributing unit; forming a sample diluent by mixing the supernatant with the diluent accommodated in the dilution chamber; supplying the sample diluent to the plurality of reaction chambers accommodating a reagent, via a distribution channel; and determining whether excessive bubbles exists in the plurality of reaction chambers by measuring the light absorption of the plurality of the reaction chambers.

The method may include: moving a sample from the sample chamber to a sample distributing unit by centrifugal force by rotating the microfluidic device using the rotation driving unit, and centrifugally separating supernatant from the sample accommodated in the sample distributing unit; forming a sample diluent by mixing the supernatant with the diluent accommodated in the dilution chamber; supplying the sample diluent to the plurality of reaction chambers accommodating a reagent, via a distribution channel; and determining whether a fluid accommodated in the plurality of reaction chambers is a sample diluent by measuring the light absorption of a reaction chamber disposed at the end of the plurality of the reaction chambers.

The method may include: obtaining at least one of the manufacturing date of the microfluidic device, the validity period of the microfluidic device, and the relationship between the detected light absorption and the concentration of components of the sample from a bar code attached to a side of the microfluidic device, using a bar code reader.

To achieve the above and/or other aspects and advantages, one or more embodiments may include a method of analyzing components contained in a sample using a microfluidic device including: a sample chamber; and at least one analyzing unit receiving a sample from the sample chamber and reacting the sample with a reagent, and measuring a light absorption of the reactant material to detect components contained in the sample, the method comprising: loading a sample into the sample chamber of the microfluidic device; moving a sample from the sample chamber to a sample distributing unit by centrifugal force, that is, by rotating the microfluidic device using the rotation driving unit, and centrifugally separating supernatant from the sample accommodated in the sample distributing unit; forming a sample diluent by mixing the supernatant with the diluent accommodated in the dilution chamber; distributing via a distribution channel the sample diluent to a plurality of chambers comprising a plurality of reaction chambers accommodating a reagent; and determining the uniformity of the dilution ratio of the sample diluent by measuring the light absorption of a chamber that is disposed in a second position from the distribution channel with respect to the chambers connected to the dilution chamber and does not contain the reagent, and the light absorption of at least one of two reaction chambers disposed at the end of the distribution channel.

BRIEF DESCRIPTION OF THE DRAWINGS

These and/or other aspects and advantages will become apparent and more readily appreciated from the following description of the embodiments, taken in conjunction with the accompanying drawings of which.

DETAILED DESCRIPTION

Figure 1:
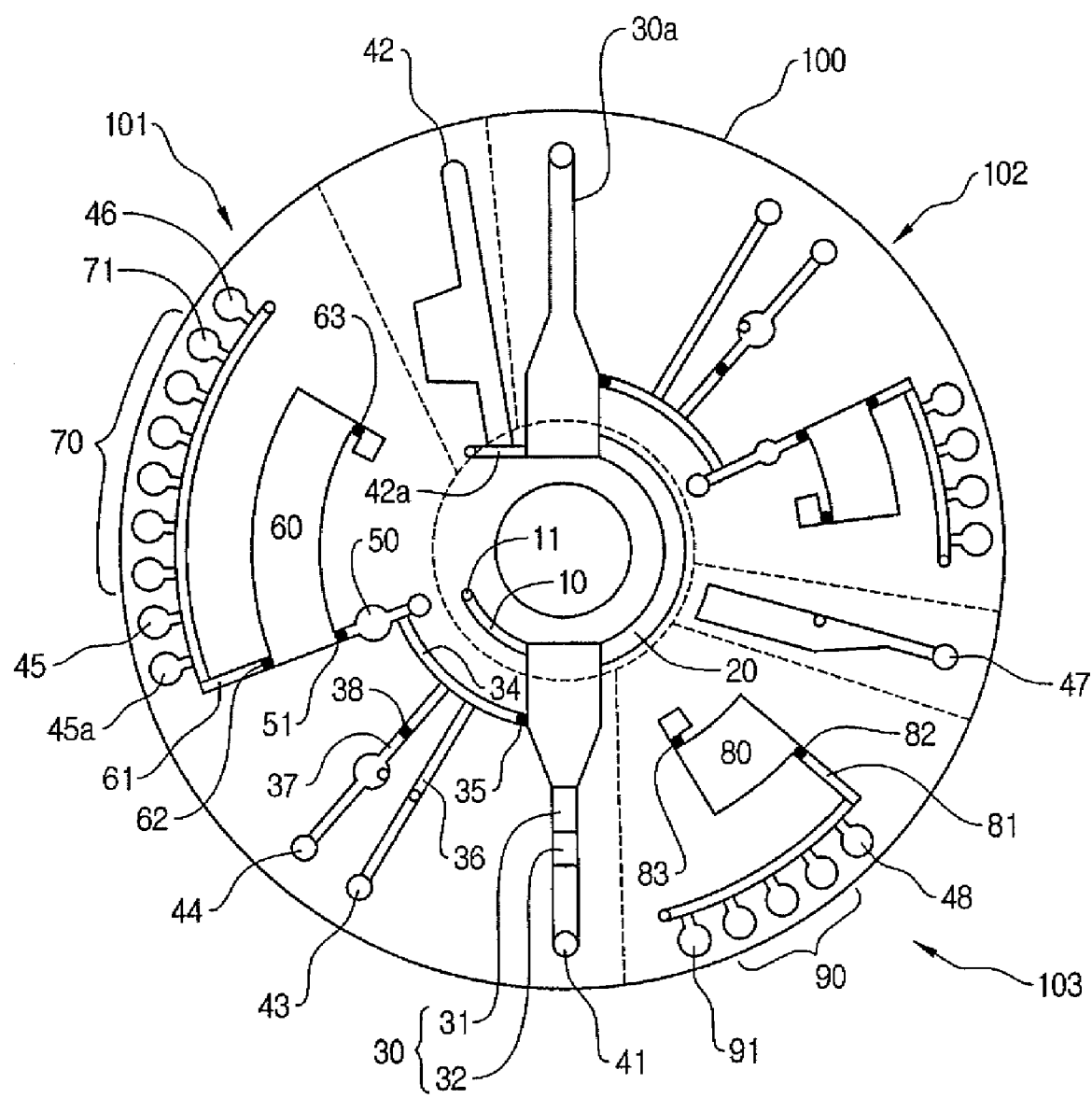
FIG. 1 is a plan view of a microfluidic device according to an embodiment.

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description.

FIG. 1 illustrates a microfluidic device according to an embodiment. Referring to FIG. 1, the microfluidic device according to the present embodiment includes a rotatable platform 100, for example, a disk-shaped platform, and microfluidic structures that provide space to accommodate fluid and channels through which the fluid can flow in the platform 100. The platform 100 can be rotated around a center C. That is, the microfluidic device can be mounted on a rotation driving unit (510 in FIG. 8) of an analyzer and be rotated. In this case, in the microfluidic structures arranged in the platform 100, samples can be moved, mixed, and so forth according to the centrifugal operation due to the rotation of the platform 100.

Figure 2:
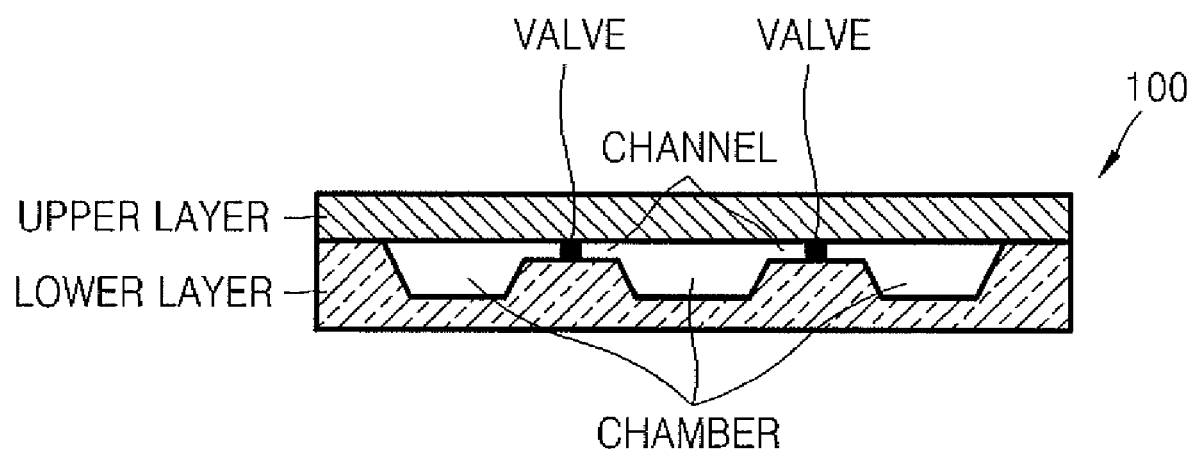
FIG. 2 is a structural diagram of a double-layered microfluidic device according to an embodiment.
Figure 3:
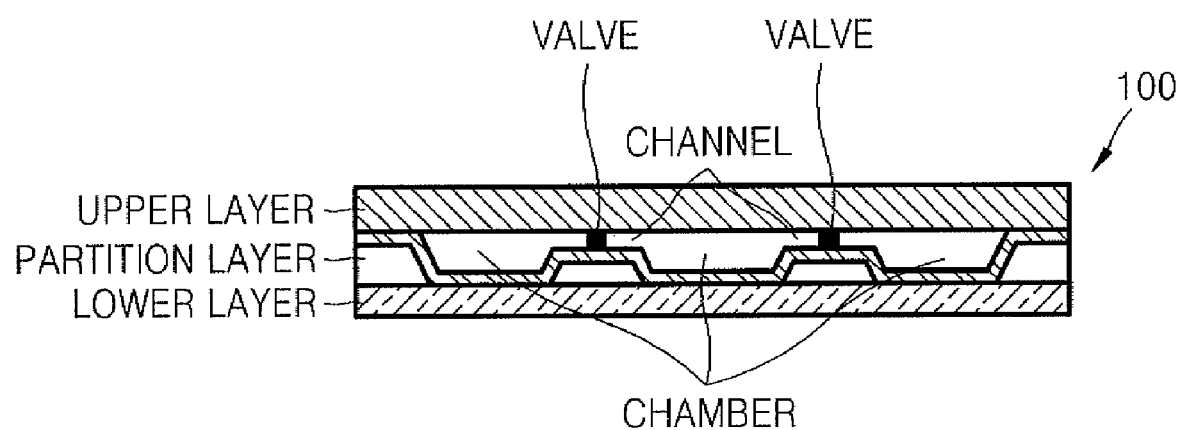
FIG. 3 is a structural diagram view of a triple-layered microfluidic device according to an embodiment.

The platform 100 may be formed of a plastic material such as acryl, polydimethylsiloxane (PDMS), or the like, which can be easily molded and has a biologically inactive surface. However, the material used to form the platform 100 is not limited thereto, and may be any material that has chemical and biological stability, optical transparency, and mechanical processibility. The platform 100 may be formed of multiple layers which may form a microfluidic structures when laminated or combined together. Depressed or sunk structures with a depth, such as chambers or channels are formed at one surface of at least one of the layers, and by bonding the layers, space and channels can be provided inside the platform 100. For example, as illustrated in FIG. 2, the platform 100 may be a double-layered structure including a lower layer and an upper layer. Also, as illustrated in FIG. 3, the platform 100 may be a structure including a partition plate for defining a space for accommodating a fluid and a flow channel through which the fluid can flow. The platform 100 may also be formed in various other ways.

When the platform 100 is formed of multiple layers, the layers may be bonded using an adhesive. For example, when the platform 100 is a double-layered structure including a lower layer and an upper layer, the lower layer and the upper layer may be bonded using an adhesive disposed between the lower layer and the upper layer. The adhesive may be a liquid material applied on the lower layer and/or the upper layer. The adhesive may be a UV (ultraviolet) curing adhesive which is cured by irradiation of UV rays. The adhesive also may be a visible light curing adhesive which is cured by irradiation of visible light rays.

The adhesive may include a curing resin and a photopolymerization initiator. The curing resin may include acrylic materials such as epoxy acrylate, urethane acrylate, polyester acrylate or silicon acrylate. The curing resin may include polyenic materials such as triarylisocyanurate or diarylmaleate, or polythiolic materials such as trimethylolpropane tris-thiopropionate. The curing resin may include epoxy resin or vinyl ether. The curing resin may also include a combination of the above materials.

The photopolymerization initiator in the UV curing adhesive may include benzoin ethers, benzophenonic materials, aminic materials, acetophenonic materials, thioxanthonic materials, Lewis acidic materials such as Lewis acid diazonium, Lewis acid sulfonium or Lewis acid iodium, or a combination thereof The photopolymerization initiator in the visible light curing adhesive may include α-diketonic materials such as camphor quinine, α-naphthyl or benzyl, 2,4-diethylthioxantone, trimethylbenzoyl diphenylsulfineoxide, methylthioxantone, or a combination thereof.

The absorption spectrum of the photopolymerization initiator may have a maximum at the wavelength of about 200 nm to about 900 nm. Further, the absorption spectrum of the photopolymerization initiator may also have a maximum at the wavelength of about 250 nm to about 600 nm.

In addition to the curing resin and the photopolymerization initiator, the adhesive may further include a sensitizer. The sensitizer may consume oxygen and provide hydrogen to the photopolymerization initiator, thereby promoting the curing reaction. For example, the sensitizer may include dimethylaminoethyl metacrylate, n-butylamine, triethylamine, 4-dimethylamino benzoic acid, isoamyl, hydrosilanic materials, sulfonylhydrazide derivative, or a combination thereof. The adhesive may further include other stabilizers, fillers, dyes, pigments, or the like.

An exemplary method of manufacturing the platform 100 using the adhesive to bond the lower layer and the upper layer will be described. The adhesive may be applied on the lower layer and/or the upper layer. The adhesive may be applied using various methods according to the viscosity of the adhesive. The adhesive having a low viscosity may be applied using an inkjet method in which an inkjet printer having at least one nozzle through which the adhesive is ejected is used. The adhesive amount ejected once through the nozzle of the inkjet printer may range between about 1 pl (picoliter) and 100 μl (microliter). However, the application method of the adhesive is not limited to the inkjet method, and other different methods may be used. That is, the adhesive having a high viscosity may be applied by a method using a silk-screen.

Next, the lower layer and the upper layer may be attached to each other, and thus the adhesive may be disposed between the lower layer and the upper layer. Electromagnetic waves may be irradiated to the adhesive. In order to irradiate light having desired wavelength to the adhesive, an optical filter may be used. The photopolymerization initiator in the adhesive may absorb light and create radicals. The radicals of the photopolymerization initiator may turn adjacent areas of the curing resin into radicals. The radicals of the curing resin may be combined to each other through polymerization, thereby bonding the lower layer and the upper layer.

The boding of the multiple layers of the platform 100 is not limited to the example of curing the adhesive using electromagnetic waves. The lower layer and the upper layer may be bonded to each other by applying suitable heat, pressure, and/or electromagnetic waves according to the adhesive.

An exemplary microfluidic structures arranged in the platform 100 will be described here by referring to FIG. 1 and other related FIGs. A sample chamber 10 is disposed closer to the center C of the platform 100. A sample is accommodated in the sample chamber 10. An opening 11 for loading a sample may be formed in the sample chamber 10.

In the platform 100, at least two sample chambers, and at least two analyzing units receiving a sample from the sample chambers and analyzing the sample may be disposed. In the present embodiment, the platform includes first and second analyzing units 101 and 102 receiving a sample from a common sample chamber, the sample chamber 10.

For example, the first and second analyzing units 101 and 102 may test items that require different dilution ratios. For example, test items for blood, such as albumin (ALB), amylase (AMY), blood urea nitrogen (BUN), calcium ($Ca^{++}$), total cholesterol (CHOL), chloride ($Cl^-$), creatine (CRE), glucose (GLU), gamma glutamyl transferase (GGT), high-concentration lipoprotein cholesterol (HDL), potassium ($K^+$), lactate dehydrogenase (LD), sodium ($Na^+$), total protein (TP), triglycerides (TRIG), and uric acid (UA) usually are diluted at about 1:100 dilution ratio of serum to diluent. Alanine aminotransferase (ALT), alanine phosphatase (ALP), aspartate aminotransferase (AST), creatine kinase (CK), direct bilirubin (D-BIL), and total bilirubin (T-BIL), usually are diluted at about 1:20 dilution ratio of serum to diluent. Accordingly, the first analyzing unit 101 may test items that are to be diluted to about 1:100 dilution ratio of serum to diluent, and the second analyzing unit 102 may test items that are to be diluted to about 1:20 dilution ratio of serum to diluent.

The first and second analyzing units 101 and 102 may also be used for testing items having the same dilution ratios. Also, the first analyzing unit 101 may test items requiring centrifugal separation, and the second analyzing unit 102 may test items that do not require centrifugal separation. The structures of the first and second analyzing units 101 and 102 are basically the same, and thus, hereinafter, the structure of just the first analyzing unit 101 will be described in detail.

Figure 4:
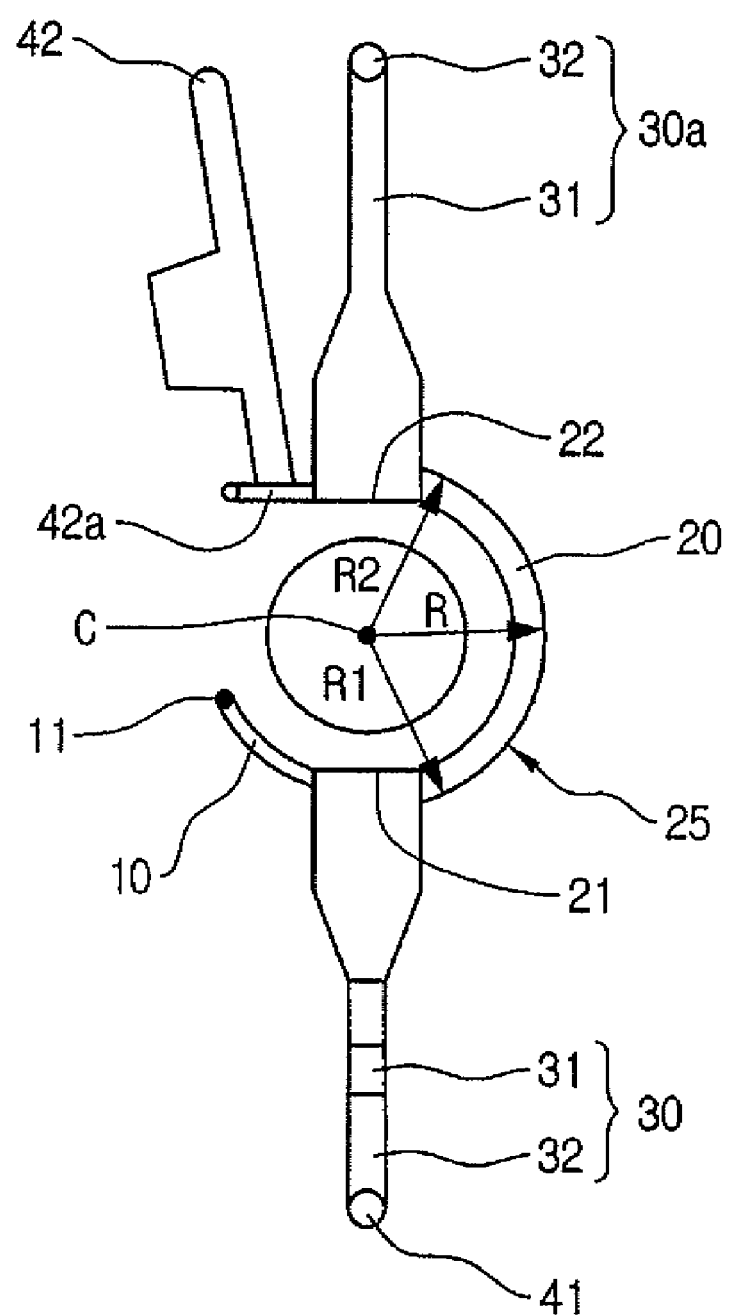
FIG. 4 is a detailed view of a sample chamber and a sample distributing unit according to an embodiment.

A sample distributing unit 30 of the first analyzing unit 101 receives a sample from the sample chamber 10, and may have a predetermined capacity for metering a certain amount of sample that is required for testing. Since centrifugal force generated by rotation of the platform 100 is used to transport the sample from the sample chamber 10 to the sample distributing unit 30, the sample distributing unit 30 is disposed farther from the center C of the platform than the sample chamber 10. The sample distributing unit 30 may function as a centrifugal separator that separates a sample, for example, blood, to supernatant and precipitations (solid substances) using the rotation of the platform 100. The sample distributing unit 30 for centrifugal separation may be formed in various manners, and examples thereof are illustrated in FIGS. 1 and 4. Referring to FIGS. 1 and 4, the sample distributing unit 30 may include a channel-shaped supernatant collecting unit 31 that is extended towards the circumference of the platform 100 in the radial direction, and a precipitation collecting unit 32 disposed at an end of the supernatant collecting unit 31 and capable of collecting precipitation having a large specific gravity.

The sample distributing unit 30 of the first analyzing unit 101 is directly connected to the sample chamber 10 to receive a sample. A sample distributing unit 30a of the second analyzing unit 102 is connected to the sample distributing unit 30 via a sample transporting unit 20. Thus, a sample is supplied from the sample chamber 10 to the sample distributing unit 30 to fill the sample distributing unit 30, and then fills the sample distributing unit 30a via the sample transporting unit 20.

Referring to FIG. 4, the sample transporting unit 20 includes a first connection portion 21 connected to the sample distributing unit 30 and a second connection portion 22 connected to the sample distributing unit 30a. The first and second connection portions 21 and 22 may be formed on an outer wall 25 of the sample transporting unit 20. A radius R2 from the center C of the platform 100 to the second connection portion 22 in the radial direction may be greater than a radius R1 from the center C of the platform 100 to the first connection portion 21. A radius of curvature R of the outer wall 25 at a point between the first and second connection portions 21 and 22 may be R1 or greater, and may gradually increase as it is towards the second connection portion 22 from the first connection portion 21. Accordingly, the sample is transported to the sample distributing unit 30 by the centrifugal force generated by the rotation of the microfluidic device to fill the sample distributing unit 30, and is then transported to the sample transporting unit 20. Then, the sample flows in the sample distribution chamber 20, initially along the inner surface of the outer wall 25 of the sample transporting unit 20 by centrifugal force and is moved to the sample distributing unit 30 via the second connection portion 22. As a plurality of sample distributing units receiving a sample from one sample chamber are formed, inconvenience of having to load a sample to each of the plurality of sample distributing units can be avoided. The term "outer wall 25" used with respect to the description of the sample transporting chamber 20 means a wall of the chamber 20 which is radially outer than other walls which configures the chamber 20.

A sample distribution channel 34 that distributes a collected supernatant, for example, serum, in the case when blood is used as a sample, to a structure for conducting a next operation is disposed at a side of the supernatant collecting unit 31. The sample distribution channel 34 is connected to the supernatant collecting unit 31 via a valve 35.

The valve 35 may be a microfluidic valve that may have various shapes. The valve 35 may be a capillary valve which is opened passively when predetermined pressure is applied, or a valve that is actively operated by receiving electromotive power or energy from the outside via operational signals. The valve 35 is a normally closed valve so that no fluid can flow through the channel 34 before absorbing electromagnetic wave energy.

Figure 5A:
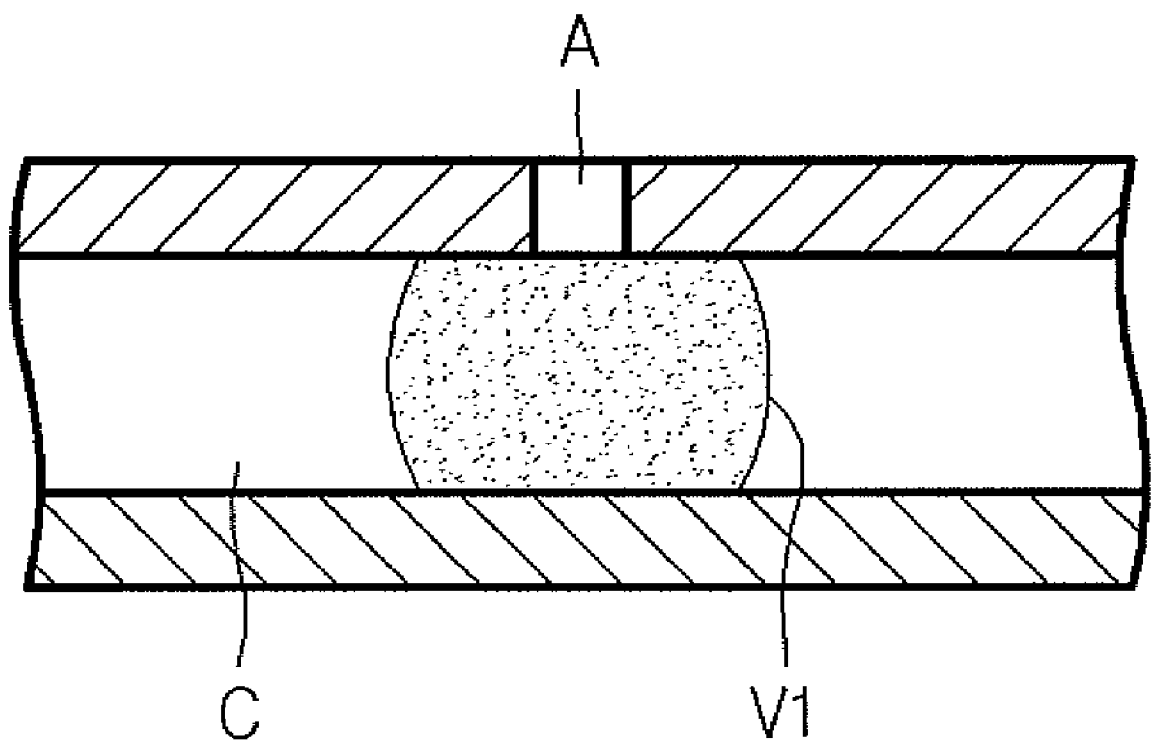
FIG. 5A is a cross-sectional view illustrating a normally closed valve, according to an embodiment.
Figure 5B:
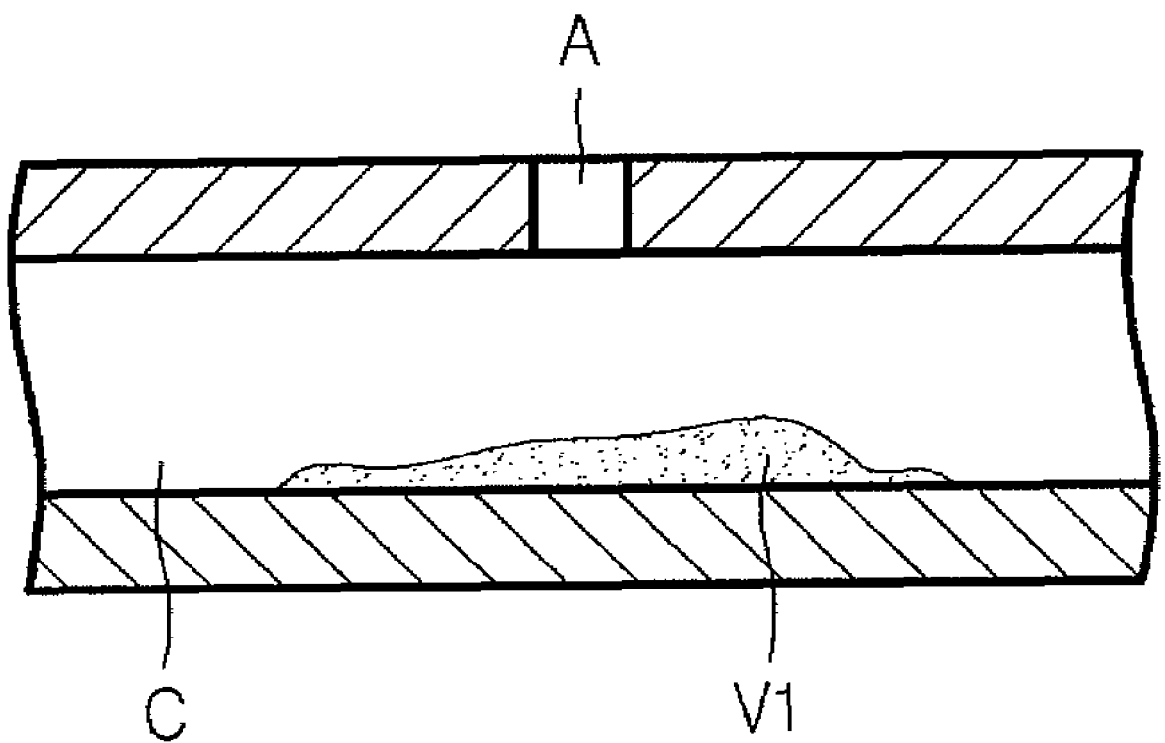
FIG. 5B is a cross-sectional view for explaining the process of opening the normally closed valve of FIG. 5A.

FIGS. 5A and 5B are cross-sectional views illustrating a normally closed valve according to an embodiment. Referring to FIG. 5A, the normally closed valve according to the present embodiment may include a valve material V1 that is in a solid state at a room temperature. The valve material V1 is disposed in a channel C and blocks the channel C as illustrated in FIG. 5A. The valve material V1 is melted at a high temperature and moved into a space inside the channel C, and is solidified again while the channel C is still opened as illustrated in FIG. 5B. Energy irradiated from an external energy source may be electromagnetic wave energy, and the external energy source may be a laser light source irradiating laser beams, a light emitting diode or a Xenon lamp irradiating visible light or infrared rays. When a laser light source is used, at least one laser diode may be included. The external energy source may be selected according to the wavelength of the electromagnetic waves that can be absorbed by heat generating particles included in the valve material V1. The valve material V1 may be a thermoplastic resin such as cyclic olefin copolymer (COC), polymethylmethacrylate (PMMA), polycarbonate (PC), polystyrene (PS), polyoxymethylene (POM), perfluoralkoxy (PFA), polyvinylchloride (PVC), polypropylene (PP), polyethylene terephthalate (PET), polyetheretherketone (PEEK), polyamide (PA), polysulfone (PSU), or polyvinylidene fluoride (PVDF). Also, the valve material V1 may be a phase change material which is solid at room temperature. In this regard, the phase change material may be wax. When heated, wax is fused, liquefied and expanded. Examples of the wax include paraffin wax, microcrystalline wax, synthetic wax, natural wax, etc. The phase change material may be a gel or thermoplastic resin. Examples of the gel include polyacrylamide, polyacrylates, polymethacrylates, polyvinylamides, etc. A plurality of minute heat generating particles that absorb electromagnetic wave energy and generate heat may be distributed in the valve material V1. The minute heat generating particles have a diameter of about 1 nm to about 100 μm so as to easily pass through the channels C which are minute, having a depth of about 0.1 mm and a width of about 1 mm. For example, the temperature of the minute heat generating particles sharply increases when electromagnetic wave energy is irradiated thereto, for example, by laser light, and thus the particles generate heat and are uniformly distributed in the wax. The minute heat generating particles may have cores including metal components and hydrophobic surface structures so as to have these properties. For example, the minute heat generating particles may include Fe-cores and an surrounding layer. The surround layer may be comprised of surfactants. The surfactant molecules may be bonded to the Fe cores. The minute heat generating particles may be dispersed in a carrier oil. The carrier oil may also be hydrophobic so that the minute heat generating particles having a hydrophobic surface structure can be uniformly dispersed. The melted phase change material may be mixed with the carrier oil dispersion of the minute heat generating particles and then the mixed material is loaded into the channel C and solidified, thereby blocking the channel C. The minute heat generating particles are not limited to the above-described polymer particles but may also be quantum dots or magnetic beads. Also, the minute heat generating particles may be metal oxides such as $Al_2O_3$, $TiO_2$, $Ta_2O_3$, $Fe_2O_3$, $Fe_3O_4$ or $HfO_2$. Meanwhile, the valve may be formed of a phase change material alone, without minute heat generating particles.

The sample distribution channel 34 is connected to a supernatant metering chamber 50 accommodating supernatant separated from the sample. The supernatant metering chamber 50 is connected to a dilution chamber 60 via a valve 51. The valve 51 may be a microfluidic valve having the same shape as the above-described valve 35.

The dilution chamber 60 accommodates a sample diluent which is a mixture of a supernatant and a diluent at a desired ratio. Thus, the term "sample diluent" used in the application means a sample adjusted to a desired concentration using a diluent. The desired concentration of the sample may be predetermined and easily determined by one skilled in the art of a biological sample analysis. A predetermined amount of dilution buffer is accommodated in the dilution chamber 60 in consideration of the dilution ratio of the supernatant to the diluent, which is usually used for the analysis of a sample. The supernatant metering chamber 50 is designed to have a capacity capable of accommodating a predetermined amount of the sample in consideration of the dilution ratio. As long as the valve 51 remains in the closed state, any of the sample cannot be introduced into the dilution chamber 60 from the supernatant metering chamber 50, even if the supernatant metering chamber is full. Accordingly, any desired amount of the sample can be supplied to the dilution chamber 60.

A plurality of reaction chambers 70 are disposed farther from the center C of the platform than the dilution chamber 60. The reaction chambers 70 are connected to the dilution chamber 60 via a distribution channel 61. Distribution of the sample diluent through the distribution channel 61 may be controlled by a valve 62. A valve 63 provides an air vent pass so that a sample diluent can be easily distributed in the reaction chambers 70. The valves 62 and 63 may be microfluidic valves having the same shape as that of the above-described valve 33.

In the reaction chambers 70, reagents suitable for different reactions with a component of the sample may be accommodated. The reagents may be loaded during the manufacture of the microfluidic device before bonding an upper layer and a lower layer for forming the platform 100. Also, instead of a closed-type reaction chamber, the reaction chambers 70 may have a vent and an opening. In the case of such a reaction chamber, the reagents may be loaded into the reaction chambers 70 before conducting the tests. The reagents may be liquid or in a lyophilized solid state.

For example, a liquid reagent may be loaded into the reaction chambers 70 before bonding upper and lower layers that form the platform 100, during the manufacture of the microfluidic device, and may simultaneously be lyophilized by a lyophilization program. Thus, by bonding the upper and lower layers, a microfluidic device containing a lyophilized reagent is provided. Alternatively, the lyophilized reagent may be accommodated in a removable case or cartridge which may be loaded into the reaction chambers 70. The lyophilized reagent may be provided by adding a filler and a surfactant to a liquid reagent and lyophilizing the mixture. The filler ensures the lyophilized reagent has a porous structure so that the lyophilized reagent can be easily dissolved when the sample diluent is loaded into the reaction chamber 70. For example, the filler may be bovine serum albumin (BSA), polyethylene glycol (PEG), dextran, mannitol, polyalcohol, myo-inositol, citric acid, ethylene diamine tetra acetic acid disodium salt (EDTA2Na), or polyoxyethylene glycol dodecyl ether (BRIJ-35). At least one or two fillers may be used. The types of the filler may depend on the type of the reagent. For example, the surfactant may be one of polyoxyethylene, lauryl ether, octoxynol, polyethylene alkyl alcohol, nonylphenol polyethylene glycol ether; ethylene oxide, ethoxylated tridecyl alcohol, polyoxyethylene nonylphenyl ether phosphate sodium salt, and sodium dodecyl sulfate. At least one or two surfactants may be added. The types of the surfactant may depend on the type of the reagent.

Figure 6:
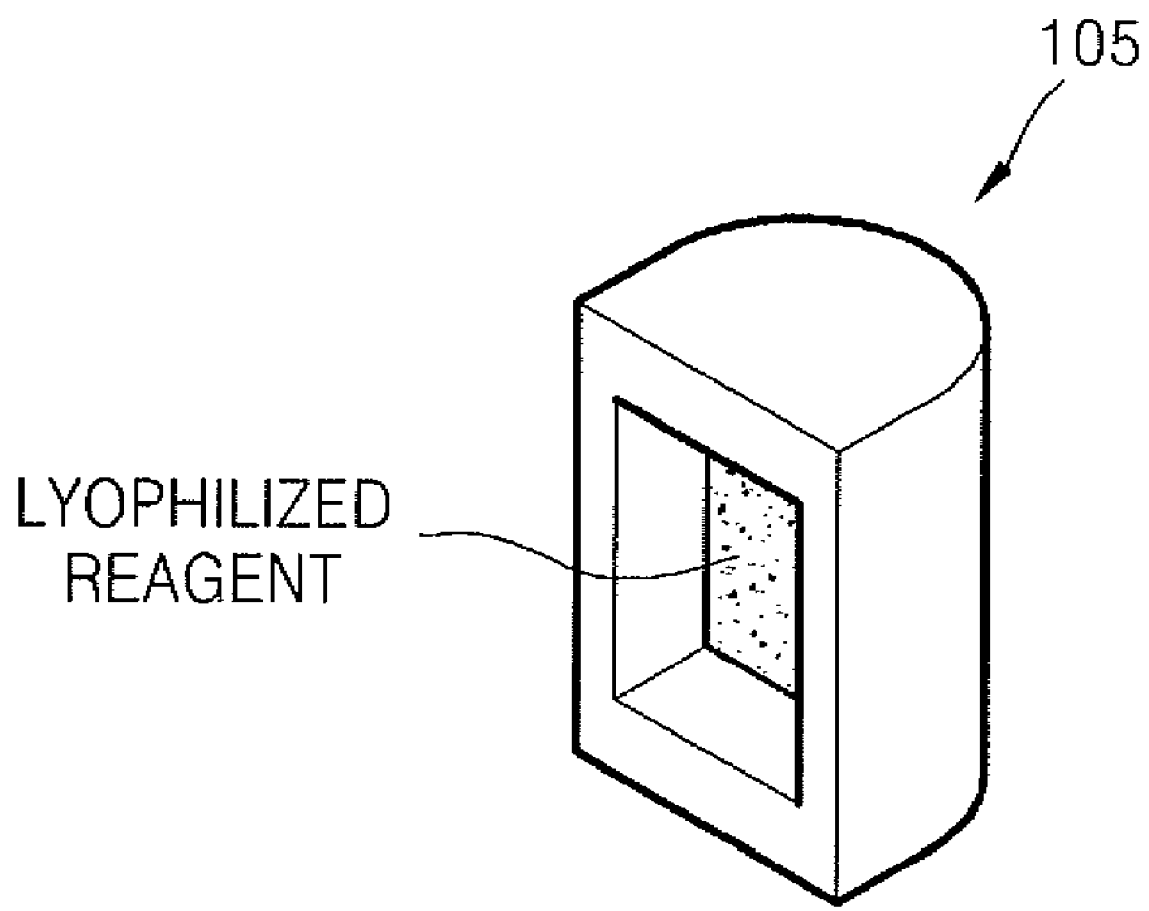
FIG. 6 is a perspective view illustrating a reagent cartridge according to an embodiment.

Also, a reagent cartridge 105 accommodating a reagent in a lyophilized state as illustrated in FIG. 6 may be disposed in (or inserted into) each of the reaction chambers 70. In this case, the reagent cartridge 105 accommodating a lyophilized reagent may be prepared in advance by subjecting a reagent cartridge 105 containing a liquid reagent to lyophilization.

A reference unit 103, which is for providing reference values and does not receive a sample from the sample chamber 10 may be disposed in the platform 100. A diluent may be stored in a dilution chamber 80 to obtain reference values when detecting reactions. A plurality of chambers 90, which are empty or contain a diluent, for obtaining detection reference values may be disposed farther away from the center C of the platform 100 than the dilution chamber 80. The chambers 90 are connected to the dilution chamber 80 via a channel 81. A valve 82 may be formed in the channel 81. A valve 83 is used to provide an air vent pass. The valves 82 and 83 may be the same as the valve 35. A chamber 91 disposed at an end of the channel 81 is for determining whether all of the chambers 90 contain a diluent.

Although not described in detail, a plurality of air vent passes for discharging air inside the microfluidic device may be disposed in the microfluidic device.

Hereinafter, chambers (which may be collectively referred to as quality control (QC) chambers) for obtaining reliable analysis results using the microfluidic device according to the current embodiment will be described with reference to FIG. 1.

A prior-use detection chamber 41 is disposed at an end of the sample distributing unit 30 to check whether the microfluidic device has been used before or not. Before supplying a sample from the sample chamber 10 to the sample distributing unit 30, it can be determined whether the microfluidic device has been previously used or not by detecting whether a sample exists in the prior-use detection chamber 41 by measuring the light absorption of the prior-use detection chamber 41 using a detector (520 in FIG. 8) which will be described later.

An excess sample chamber 42 is for determining whether a sufficient amount of sample suitable for testing is supplied to the sample distributing unit 30. The excess sample chamber may be connected to an end (usually, the end which is close toward the center of the rotation C) of the sample distributing unit of an analyzing unit via a channel. The exemplary embodiment shown in FIG. 1, the excess sample chamber 42 is connected to an upper end portion of the sample distributing unit 30a of the second analyzing unit 102 via a channel 42a. The sample of the sample chamber 10 fills the sample distributing unit 30 and then flows through the sample transporting unit 20 to fill the sample distributing unit 30a. Then the remaining sample is transported via the channel 42a to the excess sample chamber 42. After supplying a sample to the sample distributing units 30 and 30a from the sample chamber 10, in order to check whether a desired amount of sample for testing is supplied to the sample distributing units 30 and 30a, it can be determined whether a sample exists in the excess sample chamber 42 before performing a centrifugal separation, by measuring the light absorption of the excess sample chamber 42 using a detector (520 in FIG. 8) which will be described later. When at least two analyzing units that receive a sample from a single sample chamber 10 are included, the excess sample chamber 42 is connected to a sample distributing unit of an analyzing unit that receives the sample lastly. Also, when a plurality of sample chambers for supplying a sample to a plurality of analyzing units are included, a plurality of excess sample chambers connected to a sample distributing unit of each of the analyzing units may be provided.

A supernatant detection chamber 43 is connected to the sample distribution channel 34 between the supernatant collecting unit 31 of the sample distributing unit 30 and the dilution chamber 60. In one embodiment, the supernatant detection chamber 43 is connected to the sample distribution channel 34 via a channel 36. In one embodiment, the supernatant detection chamber 43 is connected to the sample distribution channel 34 between the supernatant collecting unit 31 of the sample distributing unit 30 and the excess supernatant chamber 44. When the valve 35 is opened, supernatant fills the supernatant detection chamber 43. The light absorption of the supernatant detection chamber 43 is measured using a detector (520 in FIG. 8). The operational state of the valve 35 may be checked by measuring the light absorption of the supernatant detection chamber 43. For example, if the measured light absorption indicates that the supernatant detection chamber 43 is empty, it may mean that the valve 35 did not operate properly.

The supernatant detection chamber 43 may be used to check the functional state of supernatant. A homolysis index, an icteric index, and a lipemic index may be calculated based on the measured light absorption of the supernatant detection chamber 43.

An excess supernatant chamber 44 may be connected to the sample distribution channel 34 between the supernatant collecting unit 31 and the dilution chamber. The excess supernatant chamber 44 may be connected to the sample distribution channel 34 via a channel 37. A valve 38 may be formed in the channel 37. The valve 38 is a normally closed valve like the valve 35. When the valve 38 is opened, supernatant fills the supernatant metering chamber 50 and flows into the excess supernatant chamber 44. It can be checked whether the amount of supernatant is insufficient by determining the light absorption level of the excess supernatant chamber 44.

The supernatant detection chamber 43 and the excess supernatant chamber 44 may be used as first concentration determining chambers for determining whether the dilution ratio of the sample diluent is appropriate, together with a second concentration determining chamber 45. In this case, the depths of the supernatant detection chamber 43 and the excess supernatant chamber 44 may be different. According to the Beer-Lambert Law, the light absorption is in proportion to the concentration of a sample and the length of an optical path. In other words, when the concentrations of samples are the same and the lengths of optical paths are different, the light absorption changes in proportion to the length of the optical path. Also, when the lengths of the optical path are the same and the concentrations of the sample are different, the light absorption changes in proportion to the concentrations of the sample. Since supernatant of the same concentration is accommodated both in the supernatant detection chamber 43 and the excess supernatant chamber 44, the relationship between the length of the optical path, that is, the depth of the two chambers, and the light absorption can be calculated by measuring the light absorption of the supernatant detection chamber 43 and the excess supernatant chamber 44.

The second concentration determining chamber 45 is for calculating the light absorption of the sample diluent. The second concentration determining chamber 45 is disposed at the earliest at a second position from the dilution chamber 60, among chambers connected to the dilution chamber 60 via the distribution channel 61, and receives a sample diluent via the distribution channel 61. At least one dummy chamber 45a may be disposed in front of the second concentration determining chamber 45.

A sample diluent detection chamber 46 is for determining whether a sample diluent is accommodated in all of the reaction chambers 70. No reagent is accommodated in the sample diluent detection chamber 46. The sample diluent detection chamber 46 is disposed at an end of the distribution channel 61, i.e., a location where the sample diluent is lastly distributed after all other reaction chambers receive the sample diluent. The sample diluent supplied via the distribution channel 61 is filled in the sample diluent detection chamber 46 lastly. Accordingly, by measuring the light absorption of the sample diluent detection chamber 46, it can be determined whether all of the reaction chambers 70 contain the sample diluent. For example, if a measured light absorption level of the sample diluent detection chamber 46 indicates that the sample diluent detection chamber 46 is empty, it may mean an operational defect of the valve 62.

A temperature measure chamber 47 is for ascertaining whether the temperature of a sample is suitable for carrying out a test on the sample. To this end, for example, a material whose light absorption changes in response to the temperature change thereof may be supplied to the temperature measure chamber 47. For example, a thyon dye may be supplied to the temperature measure chamber 47. By measuring the light absorption of the temperature measure chamber 47 using a detector (520 in FIG. 8) which will be described later, it can determined whether the temperature of the microfluidic device is appropriate for conducting a test. The temperature measure chamber 47 may be disposed any location on the microfluidic device.

A denaturation detection chamber 48 is for determining the storage condition of the microfluidic device. To this end, a material whose light absorption changes according to the temperature change and/or water or moisture content thereof may be accommodated in the denaturation detection chamber 48. In the current embodiment, one of the chambers 90 of the reference unit 103 is used as the denaturation detection chamber 48, but the present embodiment is not limited thereto, and two or more chambers 90 may also be used as denaturation detection chambers.

The second concentration determining chamber 45 and the sample diluent detection chamber 46 may be used together as chambers for determining whether the dilution ratio of the sample diluent is constant.

In order to minimize the motion of the detector (520 of FIG. 8), the QC chambers 41-48, the reaction chambers 70, and the chambers 90 may be disposed at the same radial distances from the center C of the platform 100.

Figure 7:
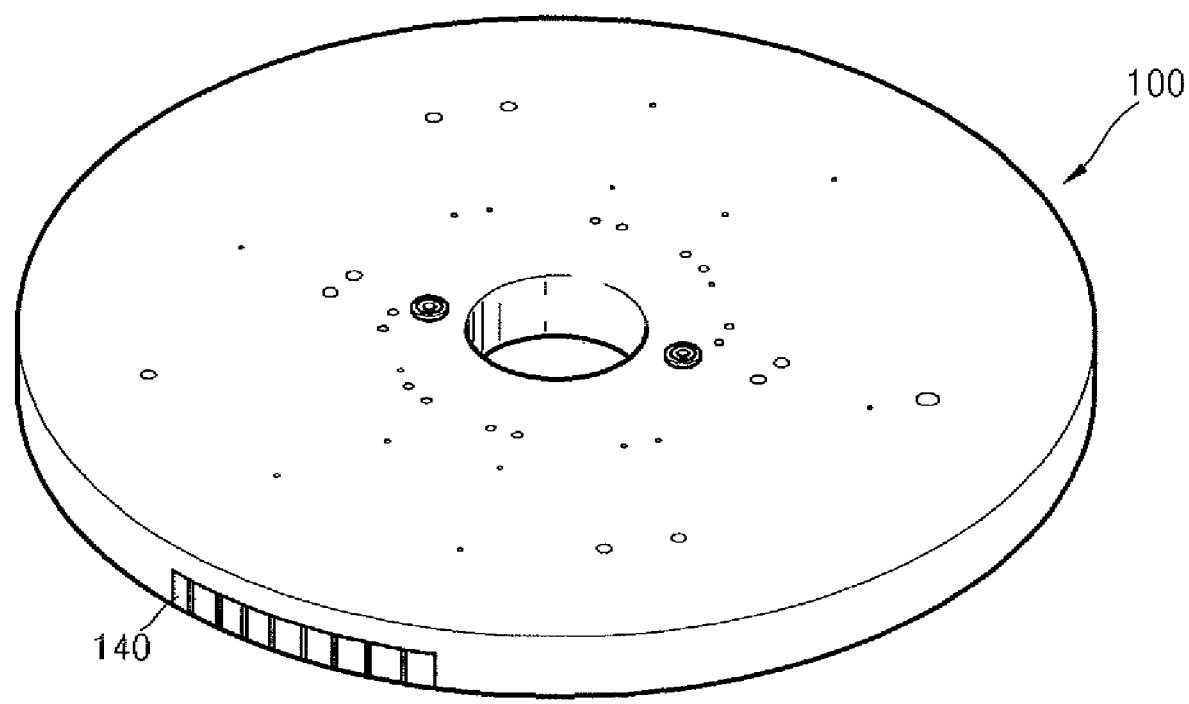
FIG. 7 is a perspective view illustrating the microfluidic device of FIGS. 1.

FIG. 7 is a perspective view of a microfluidic device according to an embodiment. Referring to FIG. 7, the microfluidic device according to the present embodiment includes a bar code 140 disposed at a side of a platform 100. The bar code 140 may be attached to a side of the platform 100. The manufacturing date of the microfluidic device and the validity period thereof may be pre-recorded in the bar code 140. Also, the bar code 140 may include data on the relationship between the level of light absorption of the reaction chambers 70 and the concentration of a material to be detected/analyzed, thus allowing an instant reading of the test results. Also, data such as homolysis index, icteric index, and lipemic index indicating the relationship between the light absorption level of the supernatant detection chamber 43 and the state of supernatant may be pre-recorded in the bar code 140.

Figure 8:
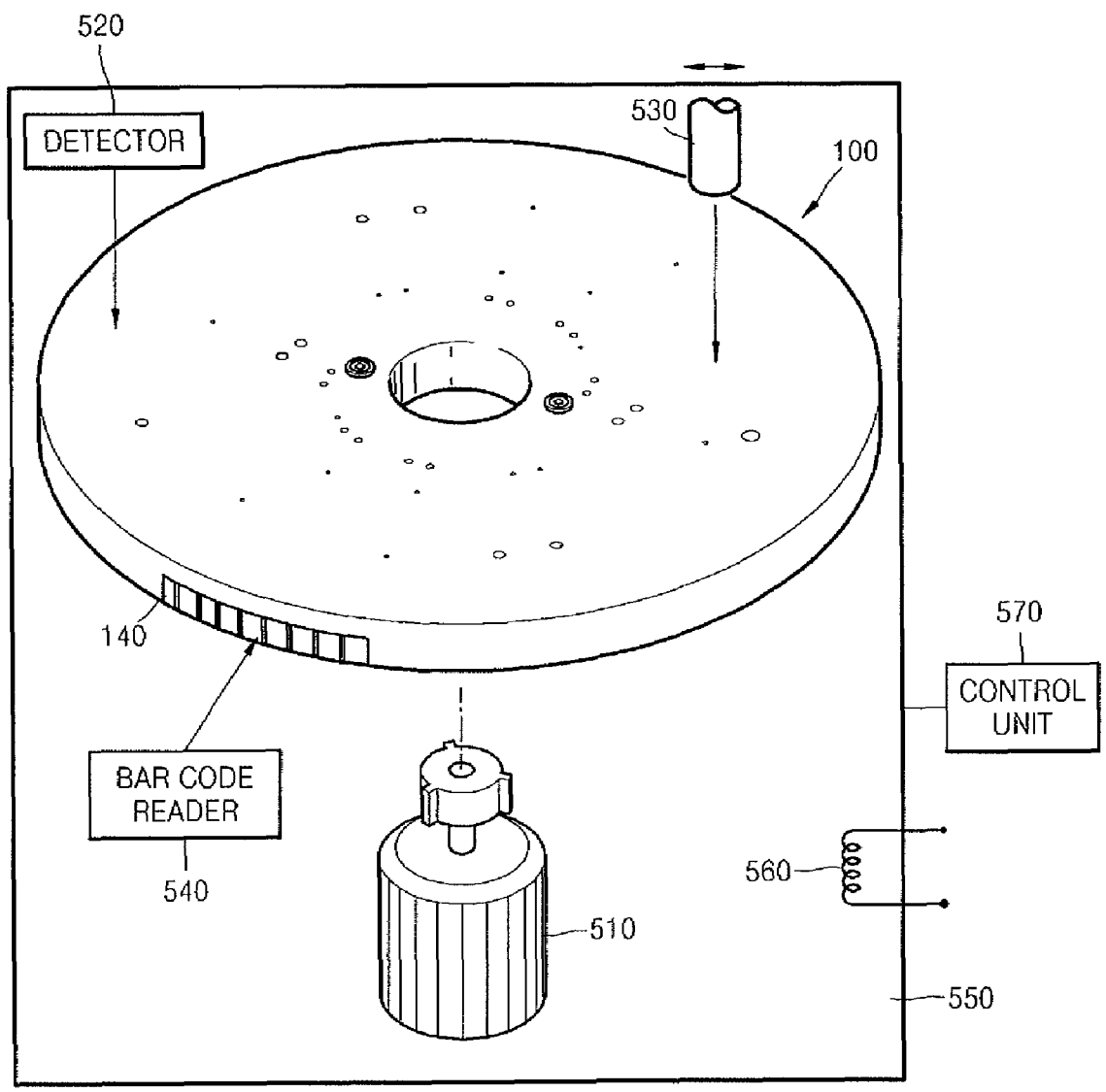
FIG. 8 illustrates a sample analysis system according to an embodiment.

FIG. 8 illustrates a sample analysis system using the microfluidic device of FIG. 1 according to an embodiment. Referring to FIG. 8, the sample analysis system using a microfluidic device according to an embodiment includes a rotation driving unit 510, a detector 520, and an electromagnetic wave generator 530. The rotation driving unit 510 rotates the microfluidic device to provide centrifugal force for centrifugal separation of a sample and movement of a fluid. The rotation driving unit 510 stops the microfluidic device at a predetermined position in order for valves of the microfluidic device to face the electromagnetic wave generator 530. The electromagnetic wave generator 530 irradiates electromagnetic waves for opening the valves, such as laser light. The electromagnetic wave generator 530 may be moved in radial directions of the microfluidic device. Also, the rotation driving unit 510 stops the microfluidic device at a predetermined position in order to align the chambers and the detector 520. Although not illustrated in FIG. 8, the rotation driving unit 510 may further comprise a motor driving unit which can control the angular position of the microfluidic device. For example, the motor driving unit may use a step motor or a direct current motor. The detector 520 detects optical characteristics such as fluorescence, luminescence, and/or absorbance, of a material to be detected. A bar code reader 540 detects a bar code formed at a side of the platform 100. The rotation driving unit 510, the detector 520, the electromagnetic wave generator 530, and the bar code reader 540 are disposed in a predetermined measuring chamber 550. A heater 560 maintains the temperature of the measuring chamber 550 to be appropriate for testing. A control unit 570 controlling the sample analysis process is disposed outside the measuring chamber 550.

Hereinafter, a method of analyzing a sample using the microfluidic device will be described. In the current embodiment, a method of analyzing blood will be described as an example.

<Supplying a Sample>

The dilution chambers 60 and 80 of the microfluidic device may contain a diluent in advance. If not, a diluent may be supplied to the dilution chambers 60 and 80 through an opening (not shown). A whole blood sample obtained from a patient is supplied to the sample chamber 10, and the microfluidic device is mounted on the rotation driving unit 510.

<Acquiring Bar Code Data>

Data of the bar code 140 at the side of the platform 100 is read using the bar code reader 540. The manufacturing date and validity period of the microfluidic device can be checked from the data pre-recorded in the bar code 140, and it can determined whether the microfluidic device is in a state for conducting an effective test by checking the validity period. If the microfluidic device is not in a state capable of conducting an effective test, the control unit 570 may generate a warning to replace the microfluidic device. Also, data pre-recorded in the bar code 140 may include data regarding the relationship between the light absorption level and concentration of a material to be analyzed, allowing an operator to apply the relationship to the measured levels of light absorption. The control unit 570 may perform such comparison and generate test results in a desired format or indicator.

<Determining Whether the Microfluidic Device has Been Used>

The light absorption of the pre-use detection chamber 41 disposed at an end of the sample distributing unit 30 is measured using the detector 520. As a result, if the measured light absorption indicates that the usage detection chamber 41 contains blood or a blood component, it means that the microfluidic device has already been used. In this case, the control unit 570 generates a warning to replace the microfluidic device.

<Determining the Storage Condition of the Microfluidic Device>

The light absorption of the denaturation detection chamber 48 is measured using the detector 520. Since a material which is denaturalized according to variation in moisture content and/or temperature and whose light absorption changes accordingly is contained in the denaturation detection chamber 48, the storage condition of the microfluidic device can be determined by detecting the light absorption of the denaturation detection chamber 48. Reagents for sample analysis contained in the reaction chambers 70 are usually maintained at a temperature of about 4° C. in order to maintain the activity of the reagents. If the reagents are not stored in suitable conditions, that is, if the reagents are stored in unsuitable conditions for a certain time period, the reagents contained in the reaction chambers 70 may lose their activity. If the storage condition of the microfluidic device is poor, the control unit 570 may generate a warning to replace the microfluidic device.

<Measurement of Temperature>

By using the detector 520, the light absorption of the temperature measure chamber 47 is measured. Since thyon dye whose light absorption changes according to the temperature is supplied to the temperature measure chamber 47, the temperature of the microfluidic device can be detected from the light absorption of the temperature measure chamber 47. The microfluidic device may be kept cold in order to maintain the activity of the reagents and the diluent. Since a microfluidic device kept cold for a certain period of time cannot be immediately used for testing, the control unit 570 generates a message indicating a low temperature and/or necessity of warming the device, when the temperature of the microfluidic device is not above a temperature appropriate for starting a test, for example, 20° C. In that case, the device may be set on standby, for example, for 1 minute. The temperature of the measuring chamber 550 can be raised by driving the heater 560. Then, an operation of measuring the temperature of the microfluidic device by measuring the light absorption of the temperature measure chamber 47 is repeated so that the microfluidic device reaches an appropriate temperature for starting a test and then the test may be conducted. The number of repetition may be set appropriately in advance, and if the desired temperature is still not reached before starting the test, the control unit 570 may generate an error or warning message.

<Determining Whether the Amount of Sample is Appropriate>

A blood sample is transported from the sample chamber 10 to the sample distributing unit 30 by rotating the microfluidic device at a low speed. In this regard, low speed refers to the rotational speed that generates proper centrifugal force to move the fluid. For example, the microfluidic device may be rotated with an acceleration of 1800 rpm/10 sec for 11 seconds. The sample is moved from the sample chamber 10 to the sample distributing unit 30 by centrifugal force. After the sample distributing unit 30 is filled, the sample is moved to the sample distributing unit 30a via the sample transporting unit 20. After the sample distributing unit 30a is filled, the blood sample is moved to the excess sample chamber 42 via a channel 42a. The detector 520 measures the light absorption of the excess sample chamber 42. The light absorption varies according to the amount of the blood sample in the excess sample chamber 42. If the amount of the blood sample is determined to be insufficient based on the measured light absorption of the excess sample chamber 42, the control unit 570 may stop the analysis and generate a warning to supply more blood sample to the sample chamber 10.

<Centrifugal Separation of Sample>

If the amount of blood sample is determined to be sufficient based on the measured light absorption of the excess sample chamber 42, the blood is centrifugally separated. The rotation driving unit 510 rotates the microfluidic device at a high speed. In this regard, high speed refers to a rotational speed at which blood can be separated into supernatant such as serum or blood plasma and precipitations such as blood corpuscles. For example, the microfluidic device may be rotated with an acceleration of 3600 rpm/10 sec for about 160 seconds. Then, heavy blood corpuscles are transported to the precipitation collecting unit 32 and the supernatant remains in the supernatant collecting unit 31.

<Metering Supernatant>

Electromagnetic waves are irradiated to the closed valve 35 using the electromagnetic wave generator 530. Then, as illustrated in FIG. 5B, the valve material V is melted and thus the valve 35 is opened. The rotation driving unit 510 rotates the microfluidic device to generate centrifugal force. Then supernatant is transported from the supernatant collecting unit 31 via the sample distribution channel 34 to the supernatant metering chamber 50 and the supernatant detection chamber 43. Since the valve 51 at the exit of the supernatant metering chamber 50 is a closed valve, the supernatant fills the supernatant metering chamber 50.

<Determining malfunction of the Valve 35>

The light absorption of the supernatant detection chamber 43 is measured using the detector 520. When the light absorption of the supernatant detection chamber 43 indicates that the supernatant detection chamber 43 is empty, it may indicate that the valve 35 is not operating properly and supernatant is not moved to the supernatant metering chamber 50 and the supernatant detection chamber 43. In this case, the process of opening the valve 35 is performed again using the electromagnetic wave generator 530 and the light absorption of the supernatant detection chamber 43 may be measured again. The number of measurement may be set appropriately. For example, when the measured light absorption indicates that the supernatant detection chamber 43 is empty after repeating the operations once, the control unit 570 may display an operating error or warning of the valve 35 and generate a warning to replace the microfluidic device.

<Determining the State of Supernatant>

When the measured light absorption indicates that the supernatant detection chamber 43 is not full or does not contain sufficient amount of supernatant, the state of the supernatant can be checked using the measured light absorption of the supernatant detection chamber 43. For example, by using the data pre-recorded in the bar code 140, homolysis index, icteric index, and lipemic index of the supernatant in the device can be calculated. These indices may be used to classify reliable results from unreliable ones.

<Determining the Amount of Supernatant>

The valve 38 disposed at an entrance of the channel 37 is opened using the electromagnetic wave generator 530. When the microfluidic device is rotated, supernatant in the supernatant collecting unit 31 and the sample distribution channel 34 flows into the excess supernatant chamber 44 by centrifugal force. The light absorption of the excess supernatant chamber 44 is measured using the detector 520. When the measured light absorption indicates that the excess supernatant chamber 44 contains a sufficient or appropriate amount of supernatant (which may be predetermined), it means that a sufficient amount of supernatant is accommodated in the supernatant metering chamber 50. When the measured light absorption indicates that the excess supernatant chamber 44 is not full and has an empty space greater than a predetermined level, it means that the amount of supernatant is not sufficient. In this case, the amount of supernatant accommodated in the supernatant metering chamber 50 may be insufficient. Also, the valve 38 may have operated poorly and thus the process of opening the valve 38 may be performed again and the light absorption of the excess supernatant chamber 44 may be measured again. The measuring operation may be repeated only once. When the repeated measurement of the light absorption indicates that the amount of supernatant is still insufficient, the control unit 570 may generate a warning to replace the microfluidic device and conduct the test again.

<Measure Reference Values for Determining Concentration of Sample Diluent>

When the light absorption of the supernatant detection chamber 43 and the excess supernatant chamber 44 are in a desired range ("normal"), the light absorption may be used to calculate a reference for detecting a concentration of the sample diluent. The light absorption depends on the amount of supernatant in the chambers 43 or 44 and the depths (length) of the supernatant detection chamber 43 and the excess supernatant chamber 44. Assuming the depths of the supernatant detection chamber 43 and the excess supernatant chamber 44 are different, the relationship between the depths of the supernatant detection chamber 43 and the excess supernatant chamber 44 and the light absorptions thereof can be calculated.

<Formation of Sample Diluent>

The valve 51 is opened using the electromagnetic wave generator 530. When the microfluidic device is rotated, supernatant is moved from the supernatant metering chamber 50 to the dilution chamber 60. The valve 63 may also be opened and form an air vent pass. The rotation driving unit 510 may move the microfluidic device in a reciprocal movement several times to mix diluent and supernatant. Thus, a sample diluent is formed in the dilution chamber 60.

<Re-Measurement of Temperature>

The temperature of the microfluidic device may be measured again. For example, analysis of a sample of a living body such as blood may be conducted at a temperature of about 37° C.±1° C. Reagents used for blood analysis are usually developed to show predetermined light absorption at the above-described temperature. Accordingly, the detector 520 detects the light absorption of the temperature measure chamber 47 to measure the temperature. When the temperature does not reach about 37° C.±1° C., the control unit 570 generates a message for warming or heating and waits on standby. Here, the temperature of the measuring chamber 550 is raised by driving the heater 560. Then the light absorption of the temperature measure chamber 47 is repeatedly detected to measure the temperature of the microfluidic device. When the temperature of the microfluidic device reaches about 37° C.±1° C., the test can be conducted continuously. The number of re-measurement of the temperature may be set appropriately, for example, once. If the temperature of the microfluidic device does not reach about 37° C.±1° C., despite repeated measurements, the control unit 570 may generate a temperature error or warning message and end or stop the test. Also, the control unit 570 may generate a warning to replace the microfluidic device.

<Distributing the Sample Diluent>

The valve 62 is opened using the electromagnetic wave generator 530. When the microfluidic device rotates, the sample diluent fills, via the distributing channel 61, the excess supernatant chamber 45, the reaction chambers 70, and the sample diluent detection chamber 46. Also, the valves 82 and 83 are opened using the electromagnetic wave generator 530. When the microfluidic device rotates, a diluent in the dilution chamber 80 fills the chamber 90 via the channel 81.

<Determining Distribution of Sample Diluent>

The light absorption of the sample diluent detection chamber 46 disposed at the end of the channel 61 where the sample diluent is lastly distributed from the distributing channel 61, is measured using the detector 520. When the light absorption indicates that a sample diluent exists in the sample diluent detection chamber 46, it means the sample diluent has filled the reaction chambers 70 completely. When the measured light absorption indicates an empty state of the reaction chambers 70, the valve 62 may have operated poorly. In this case, the process of opening the valve 62 is performed again and the light absorption of the sample diluent detection chamber 46 is measured again. Also, when measuring the light absorption again, the processes of opening the valve 51 and the valve 62 may be performed again. If the sample diluent detection chamber 46 is determined to be empty at a second repeated measurement or after, the control unit 570 may generate a warning to replace the microfluidic device. The number of re-measurements again may be set to be once, for example.

The light absorption of the chamber 91 disposed at the end of the channel 81 where the dilution is distributed lastly in the reference unit 90 is measured using the detector 520. When the light absorption indicates that the chamber 91 contains a diluent, it may mean the diluent has filled the chamber 91. When the measured light absorption indicates that the chamber 91 is empty, the valve 62 may have operated poorly. In this case, the process of opening the valve 82 is performed again and the light absorption of the chamber 91 is measured again. If the chamber 91 is determined to be still empty, the control unit 570 may generate a warning to replace the microfluidic device. The frequency of re-measurements may be set to be once, for example.

<Detecting malfunction of the Valve 51>

The light absorption of the reaction chamber 71 disposed at the end of the reaction chambers 70, where the sample diluent is distributed lastly, is measured using the detector 520. When the measured light absorption indicates that the reaction chamber 71 contains only a diluent, it means that supernatant is not mixed with the diluent due to the malfunction of the valve 51. Since only diluent is accommodated in the chamber 91 of the reference unit 103, when the light absorption of the reaction chamber 71 is the same as that of the chamber 91, it means that only diluent exists in the reaction chamber 71 as well. In this case, the control unit 570 may generate an error or warning message and end or stop the analysis.

<Measuring the Light Absorption for Analysis>

The rotation driving unit 510 may move the microfluidic device in a reciprocal movement in order to mix a sample diluent and a reagent. Then, the light absorption of the reaction chambers 70, the second concentration measure chamber 45, and as necessary, that of the chambers 90 of the reference unit 103 are measured. The endpoint of a reaction in each of the chambers may be determined by measuring the light absorption repeatedly measured at certain time intervals to check the light absorption of the chambers until the reaction reaches the end. Concentration of a component to be detected for each of a plurality of analysis items is calculated using the relationship between the light absorption pre-recorded in the bar code 140 and the concentration of the component to be detected.

<Determining Dilution Ratio>

It is determined whether the dilution ratio of the sample diluent is appropriate by using the light absorption of the second concentration measure chamber 45, the supernatant detection chamber 43, and/or the excess supernatant chamber 44. For example, when a sample having a concentration C is put into a chamber having a depth L1, and a light absorption value of the sample is A1; when the same sample having the concentration C is put into a chamber having a depth L2, the light absorption value A2 of the sample is $(L2/L1)A1$. For example, when L1 is 6 mm and L2 is 1.2 mm, A2 is $(1/5)A1$. Also, when L1 is 6 mm and L2 is 0.6 mm, A2 is $(1/10)A1$. Then, by using a sample having a concentration C, a sample diluent is formed to have a 1:B dilution ratio of the sample to a diluent. The sample diluent is then accommodated in a chamber having a depth L3, and a light absorption value of the sample diluent here is referred to as A3. The concentration of the sample in the sample diluent is C/B, and since the light absorption value is in proportion to the length of the optical path, A3 is $(1/B)(L3/L1)A1$. For example, when $L1=L3=6$ mm and $B=100$, A3 is $(1/100)A1$. Also, when $L1=6$ mm, $L3=1.2$ mm, and $B=100$, A3 is $(1/100)(1/5)A1=(1/500)A1$. Also, when $L1=L3=6$ mm and $B=20$, A3 is $(1/20)A1$. Also, when $L1=6$ mm, $L3=1.2$ mm, and $B=20$, A3 is $(1/20)(1/5)A1=(1/100)A1$. Accordingly, when the light absorption of the second concentration measure chamber 45, the supernatant detection chamber 43, and/or the excess supernatant chamber 44 are already known, the light absorption value of the sample diluent can be calculated even when the concentration of supernatant itself is not known.

While the depths (or lengths) of the supernatant detection chamber 43, the excess supernatant chamber 44, and the second concentration detection chamber 45 are determined during the manufacture of the microfluidic device and thus are already known, the light absorption value of the sample diluent having a known dilution ratio can be calculated by measuring the light absorption value of the supernatant in the supernatant detection chamber 43 and the excess supernatant chamber 44. Accordingly, when the light absorption value measured in the second concentration measure chamber 45 is identical to or within the allowable error range of the light absorption value estimated from the light absorption value measured in the supernatant detection chamber 43 and the excess supernatant chamber 44, the dilution ratio of the sample diluent can be determined to be appropriate, and the result of the test is also reliable. Also, the dilution ratio of the sample diluent can be calculated from the light absorption value measured in the second concentration measure chamber 45 and the light absorption value measured in the supernatant detection chamber 43 and the excess supernatant chamber 44, and when the calculated dilution ratio of the sample diluent is identical to or within the allowable error range of a desired dilution ratio, the test result may be considered to be reliable. According to the above-described method, the dilution ratio of the sample diluent can be measured just from the light absorption value and the length of the optical path even when the concentration of the sample (supernatant) is not known, and the reliability of the test can be ascertained. Also, the dilution ratio of the sample diluent may be determined by calculating the relationship between the concentration and depth of supernatant from the light absorption of the supernatant detection chamber 43 and the excess supernatant chamber 44 and using the light absorption and depth of the second concentration measure chamber 45.

<Determining the Dilution Uniformity>

The light absorption of the second concentration detection chamber 45 and the light absorption of the sample dilution detection chamber 46 or the reaction chamber 71 disposed at the end of the reaction chambers 70 are compared. If the light absorption of the second concentration detection chamber 45 and the sample dilution detection chamber 46 or the reaction chamber 71 are identical, it means that the dilution ratios of the sample diluent accommodated in all of the reaction chambers 70 are almost the same, and the result of the analysis in this case may be considered accurate. When supernatant and diluent are not uniformly mixed in the dilution chamber 60, the light absorption value of the second concentration detection chamber 45 and the sample diluent detection chamber 46 or the reaction chamber 71 may differ from each other.

<Checking bubbles of the Reaction Chamber>

When the light absorption of the reaction chambers 70 and of the chambers of the reference unit 103 indicate that excessive bubbles exist therein, an error message is generated regarding the test item in which bubbles are generated. A significant fluctuation of light absorption of a sample or a chamber may be an indication of presence of excessive bubbles. Thus, the light absorption measurement of the chambers can be used to determine whether excessive bubbles exist or not.

It should be understood that the exemplary embodiments described therein should be considered in a descriptive sense only and not for purposes of limitation. Descriptions of features or aspects within each embodiment should typically be considered as available for other similar features or aspects in other embodiments.

What is claimed is:

1. A microfluidic device comprising:
   a sample chamber;
   at least one analyzing unit receiving a sample from the sample chamber and detecting a component contained in the sample according to a reaction between the sample and a reagent; and
   a denaturation detection chamber determining at least one of a temperature and a moisture content of the microfluidic device are in a predetermined range, wherein the denaturation detection chamber accommodates a material whose light absorption changes according to the temperature and/or the moisture content thereof.

2. The microfluidic device of claim 1, wherein the respective at least one analyzing unit comprises:
   a sample distributing unit connected to the sample chamber and separating supernatant from the sample;
   a dilution chamber connected to the sample distributing unit, wherein the dilution chamber accommodates a diluent for diluting the supernatant; and
   a plurality of reaction chambers connected parallel to the dilution chamber via a common distribution channel to receive a sample diluent, said common distribution channel having a first end and a second end, wherein the individual reaction chambers accommodate a reagent; and wherein the sample diluent flows in the distribution channel from the first end toward the second end.

3. The microfluidic device of claim 2, further comprising a supernatant metering chamber which meters the supernatant supplied from the sample distributing unit, said supernatant metering chamber is disposed between the sample distribution unit and the dilution chamber and fluid communicates to the sample distribution unit and to the dilution chamber through a channel.

4. The microfluidic device of claim 2, further comprising a prior-use detection chamber used to determine whether the microfluidic device has been used before or not by measuring light absorption of the prior-use detection chamber,
   wherein the prior-use detection chamber is fluid connected to the sample chamber or the sample distributing unit.

5. The microfluidic device of claim 2, further comprising an excess sample chamber used to determine the amount of the sample by measuring light absorption of the excess sample chamber and accommodating an excess amount of the sample exceeding the capacity of the sample distributing unit, wherein the excess sample chamber is fluid communicate with the sample distributing unit.

6. The microfluidic device of claim 3, further comprising a supernatant detection chamber used to determine the state of the supernatant by measuring light absorption of the supernatant detection chamber and which is connected to the channel that connects the supernatant metering chamber and the sample distributing unit.

7. The microfluidic device of claim 3, further comprising an excess supernatant chamber that is disposed between the supernatant metering chamber and the sample distributing unit and is connected to the channel that connects the supernatant metering chamber and the sample distributing unit, said excess supernatant accommodating an excessive amount of supernatant exceeding the capacity of the supernatant metering chamber.

8. The microfluidic device of claim 2, further comprising at least one first concentration determining chamber that is used to provide a reference value for determining the concentration of the sample diluent by measuring light absorption of the first concentration measure chamber and receives supernatant from the sample distributing unit.

9. The microfluidic device of claim 8, comprising at least two of the first concentration determining chambers, wherein the lengths of the at least two first concentration determining chambers are different.

10. The microfluidic device of claim 2, further comprising a second concentration determining chamber that is connected to the distribution channel and receiving a sample diluent from the dilution chamber, wherein the second concentration determining chamber is connected to the distribution channel at a position to receive the sample diluent prior to the plurality of reaction chamber; wherein the device further comprises a dummy chamber disposed between the second concentration determining chamber and the dilution chamber, said dummy chamber receives the sample diluent prior to the second concentration determining chamber; and wherein the second concentration determining chamber is used to determine the concentration of the sample diluent by measuring the light absorption of the second concentration detection chamber.

11. The microfluidic device of claim 2, further comprising a sample diluent detection chamber that is connected to the distribution channel at the second end of the distribution channel and receives the sample diluent after all of the plurality of reaction chambers receive the sample diluent.

12. The microfluidic device of claim 2, further comprising a plurality of reagent cartridges accommodating the reagent in a lyophilized state and installed in the respective reaction chambers.

13. The microfluidic device of claim 1, further comprising a temperature detection chamber accommodating a material whose light absorption changes according to the temperature thereof.

14. The microfluidic device of claim 1, further comprising:
   a platform comprising a first layer and a second layer which are bonded to face other; and
   an adhesive disposed between the first layer and the second layer to bond the first layer and the second layer to each other,
   wherein the sample chamber, the at least one analyzing unit and the denaturation detection chamber are formed as grooves in the first layer.

15. The microfluidic device of claim 14, wherein the adhesive is cured by irradiation electromagnetic waves.

16. The microfluidic device of claim 14, wherein the adhesive comprises a photopolymerization initiator the absorption spectrum of which has a maximum at the wavelength of about 200 nm to about 900 nm.

17. The microfluidic device of claim 16, wherein the adhesive comprises a photopolymerization initiator the absorption spectrum of which has a maximum at the wavelength of about 250 nm to about 600 nm.

18. The microfluidic device of claim 14, wherein the adhesive comprises a curing resin and a photopolymerization initiator.

19. The microfluidic device of claim 18, wherein the photopolymerization initiator is selected from the group consisting of benzoin ethers, benzophenonic materials, aminic materials, acetophenonic materials, thioxanthonic materials, Lewis acidic materials, and a combination thereof.

20. The microfluidic device of claim 18, wherein the photopolymerization initiator is selected from the group consisting of camphor quinine, α-naphthyl, benzyl, 2,4-diethylthioxantone, trimethylbenzoyl diphenylsulfineoxide, methylthioxantone, and a combination thereof.

21. A method of manufacturing the microfluidic device of claim 1, the method comprising:

providing a first layer comprising grooves which correspond to the sample chamber, the at least one analyzing unit, and the denaturation detection chamber, respectively;

providing a second layer;

applying an adhesive on the first layer and/or the second layer;

attaching the first layer and the second layer to each other; and curing the adhesive by irradiating light to the adhesive.

22. The method of claim 21, wherein the curing the adhesive comprises irradiating an electromagnetic wave to the adhesive.

23. The method according to claim 21, wherein the curing the adhesive comprises irradiating light having wavelength of about 200 nm to about 900 nm or selectively irradiating light having any wavelength band using an optical filter.

24. A method of analyzing components contained in a sample using a microfluidic device comprising: a sample chamber; and at least one analyzing unit receiving a sample from the sample chamber and forming a reaction mixture of the sample and a reagent, and measuring a light absorption of the reaction mixture in order to detect components contained in the sample, the method comprising:

supplying a sample to the sample chamber of the microfluidic device;

mounting the microfluidic device on a rotation driving unit; and determining whether at least one of a temperature and a moisture content of the microfluidic device is in a predetermined range by measuring the light absorption of a denaturation detection chamber of the microfluidic device; wherein the denaturation detection chamber contains a material whose light absorption changes according to temperature and/or moisture content thereof.

25. The method of claim 24, comprising:

moving a sample from the sample chamber to a sample distributing unit by centrifugal force by rotating the microfluidic device using the rotation driving unit; and determining whether the microfluidic device has been used before by measuring the light absorption of a prior-use detection chamber that is in fluid communication with the sample chamber or the sample distributing unit.

26. The method of claim 24, comprising:

moving a sample from the sample chamber to a sample distributing unit by centrifugal force; and determining whether the amount of the sample is sufficient by measuring the light absorption of the excess sample chamber which accommodates an excessive sample exceeding the capacity of the sample distributing unit.

27. The method of claim 26, wherein, when the microfluidic device comprises a plurality of the at least one analyzing unit that receive a sample from the sample chamber, a sample exceeding the capacity of the sample distributing unit of a final analyzing unit of the plurality of analyzing units is accommodated in the excess sample chamber.

28. The method of claim 24, comprising determining whether the temperature of the microfluidic device is suitable for a test by measuring the light absorption of the denaturation detection chamber which accommodates a material whose light absorption changes according to the temperature thereof, wherein the determining is performed using a detector.

29. The method of claim 24, comprising:

moving a sample from the sample chamber to a sample distributing unit by centrifugal force, and centrifugally separating supernatant from the sample accommodated in the sample distributing unit; and detecting at least one of an index indicating the status of the supernatant and whether a valve disposed at an exit of the sample distributing unit has an operational defect by measuring the light absorption of the supernatant detection chamber which receives supernatant from the sample distributing unit.

30. The method of claim 29, comprising:

metering an amount of supernatant that flows from the sample distributing unit into the supernatant metering chamber;

moving an excessive amount of supernatant exceeding the capacity of the supernatant metering chamber to the excess supernatant chamber; and determining whether the amount of the supernatant is sufficient by measuring a light absorption of the excess supernatant chamber.

31. The method of claim 24, comprising:

moving a sample from the sample chamber to a sample distributing unit by centrifugal force and separating supernatant from the sample accommodated in the sample distributing unit;

measuring a light absorption of at least one first concentration determining chamber which receives supernatant from the sample distributing unit;

forming a sample diluent by mixing the supernatant with a diluent accommodated in the dilution chamber;

supplying via a distribution channel the sample diluent to a second concentration determining chamber, and measuring light absorption of the second concentration detection chamber; and determining whether the dilution ratio of the sample diluent is in a predetermined range, said determination being carried out using the measured light absorption and depths of the first and second concentration detection chambers, wherein the second concentration determining chamber is located between the dilution chamber and reaction chambers where the sample diluent are brought into contact with the reagent; and wherein and the second concentration determining chamber is in fluid communication with the dilution chamber and reaction chambers.

32. The method of claim 24, comprising:

moving a sample from the sample chamber to a sample distributing unit by centrifugal force and centrifugally separating supernatant from the sample accommodated in the sample distributing unit;

forming a sample diluent by mixing the supernatant with the diluent accommodated in the dilution chamber;

supplying via a distribution channel the sample diluent to a second concentration determining chamber, a plurality of reaction chambers accommodating a reagent, and a sample diluent detection chamber, which are sequentially disposed; and measuring the light absorption of the second concentration determining chamber and the light absorption of at least one of the sample diluent detection chamber and a reaction chamber disposed at the end of the plurality of reaction chambers to determine whether the dilution ratio of the sample diluent distributed to respective reaction chambers is consistent.

33. The method of claim 24, comprising:

moving a sample from the sample chamber to a sample distributing unit by centrifugal force and centrifugally separating supernatant from the sample accommodated in the sample distributing unit;

forming a sample diluent by mixing the supernatant with the diluent accommodated in the dilution chamber;

supplying the sample diluent to a plurality of reaction chambers accommodating a reagent, via a distribution channel; and determining whether excessive bubbles exists in the plurality of reaction chambers by measuring the light absorption of the plurality of the reaction chambers.

34. The method of claim 24, comprising:

moving a sample from the sample chamber to a sample distributing unit by centrifugal force centrifugally separating supernatant from the sample accommodated in the sample distributing unit;

forming a sample diluent by mixing the supernatant with the diluent accommodated in the dilution chamber;

supplying the sample diluent to a plurality of reaction chambers accommodating a reagent, via a distribution channel; and determining whether a fluid accommodated in the plurality of reaction chambers is the sample diluent by measuring the light absorption of the reaction chamber disposed at the location where said reaction chamber receives the sample diluent lastly after all other of the plurality of the reaction chambers receive the sample diluent.

35. The method of claim 24, comprising:

determining at least one information of the manufacturing date of the microfluidic device, the expiration date of the microfluidic device, and the relationship between the detected light absorption and the concentration of components of the sample, wherein the information is pre-recorded in a bar code attached to a surface of the microfluidic device; and wherein the determination is carried out by reading the bar code.

36. A method of analyzing components contained in a sample using a microfluidic device comprising: a sample chamber; and at least one analyzing unit receiving a sample from the sample chamber and allowing the sample to react with a reagent, and measuring a light absorption of the reactant material to detect components contained in the sample, the method comprising:

loading a sample into the sample chamber of the microfluidic device;

moving a sample from the sample chamber to a sample distributing unit by centrifugal force and centrifugally separating supernatant from the sample accommodated in the sample distributing unit;

forming a sample diluent by mixing the supernatant with the diluent accommodated in the dilution chamber;

distributing via a distribution channel the sample diluent to a plurality of chambers comprising a plurality of reaction chambers each accommodating a reagent; and determining the uniformity of the dilution ratio of the sample diluent by measuring the light absorption of a chamber that is disposed in a second position from the distribution channel with respect to the chambers connected to the dilution chamber and does not contain the reagent, and the light absorption of at least one of two reaction chambers disposed at the end of the distribution channel.

37. A microfluidic device suitable for analyzing a fluid sample to detect a component contained in the sample, comprising a sample chamber which receives the sample;

a sample distribution chamber which receives the sample and separates the sample into a fluid supernatant and a solid substance;

a plurality of reaction chambers where the supernatant is brought into contact with a reagent, the reaction chambers being in fluid communication with the sample chamber via a channel and receiving the supernatant through the channel; and a quality control chamber, wherein the quality control chamber is one or more selected from the group consisting of:

a temperature measure chamber which accommodates a material of which light absorbance changes depending on the temperature;

a chamber which accommodates a material of which light absorbance changes depending on a level of the supernatant supplied to the reaction chamber to determine the level of the supernatant supplied to the reaction chambers;

a chamber which accommodates a material of which light absorbance changes depending on a functional state of the supernatant to determine the functional state of the supernatant;

a chamber which accommodates a material of which light absorbance changes depending on a consistency of the concentration of the supernatant in the reaction chambers to determine the consistency of the concentration of the supernatant in the reaction chambers;

a chamber which accommodates a material of which light absorbance changes depending on a level of the supernatant supplied to the reaction chamber to determine the level of the sample in the sample distribution chamber; and a prior-use determining chamber which is connected to the sample chamber or sample distribution chamber and which accommodates a material of which light absorbance changes depending on whether the device is previously used to determine whether the device is previously used.

\* \* \* \* \*